United States Patent [19]

Gehrmann et al.

[11] Patent Number: 4,560,518

[45] Date of Patent: Dec. 24, 1985

[54] PROCESS FOR THE CONTINUOUS PRODUCTION OF 2-CARBOXYETHYL-ALKYL-PHOSPHINIC ACID DIALKYLESTERS

[75] Inventors: Klaus Gehrmann; Alexander Ohorodnik, both of Erftstadt; Johannes Rosenthal, Cologne, all of Fed. Rep. of Germany

[73] Assignee: Hoechst Aktiengesellschaft, Fed. Rep. of Germany

[21] Appl. No.: 554,593

[22] Filed: Nov. 23, 1983

[30] Foreign Application Priority Data

Dec. 8, 1982 [DE] Fed. Rep. of Germany ....... 3245364

[51] Int. Cl.$^4$ ................................................ C07F 9/32
[52] U.S. Cl. ..................................... 260/970; 260/941
[58] Field of Search .......................................... 260/970

[56] References Cited

U.S. PATENT DOCUMENTS 2,724,718 11/1955 Stiles et al. ........................... 260/970
2,971,019 2/1961 Ladd et al. ........................... 260/970

OTHER PUBLICATIONS

Pudovik et al., *Izvest. Akad. Nauk. SSSR, Otdel. Khim. Nauk*, [1952], 803–806.

*Primary Examiner*—Anton H. Sutto
*Attorney, Agent, or Firm*—Connolly and Hutz

[57] ABSTRACT

The disclosure relates to a process for the continuous production of 2-carboxyethyl-alkyl-phosphinic acid dialkylesters by reacting an alkanephosphonous acid monoalkylester with an acrylic acid ester in the presence of a metal alcoholate. To this end, the disclosure provides:

(a) for a quantity by volume (corresponding to the reactor volume) of 2-carboxyethyl-alkyl-phosphinic acid dialkylester which is to be produced, to be introduced into a reactor adapted to circulate reaction mixture therein, closed in itself and provided with cooling means and an overflow, and circulated in the reactor;

(b) for the alkanephosphonous acid monoalkylester, acrylic acid alkylester and an alcoholic solution of the metal alcoholate to be continuously introduced into the reactor while cooling the material circulated therein, and for the whole to be reacted at a temperature of about 0° to 80° C.; and (c) for a mixture containing final product to be continuously removed through the overflow of the reactor and for 2-carboxyethyl-alkyl-phosphinic acid dialkylester to be distillatively separated from the mixture.

8 Claims, 1 Drawing Figure

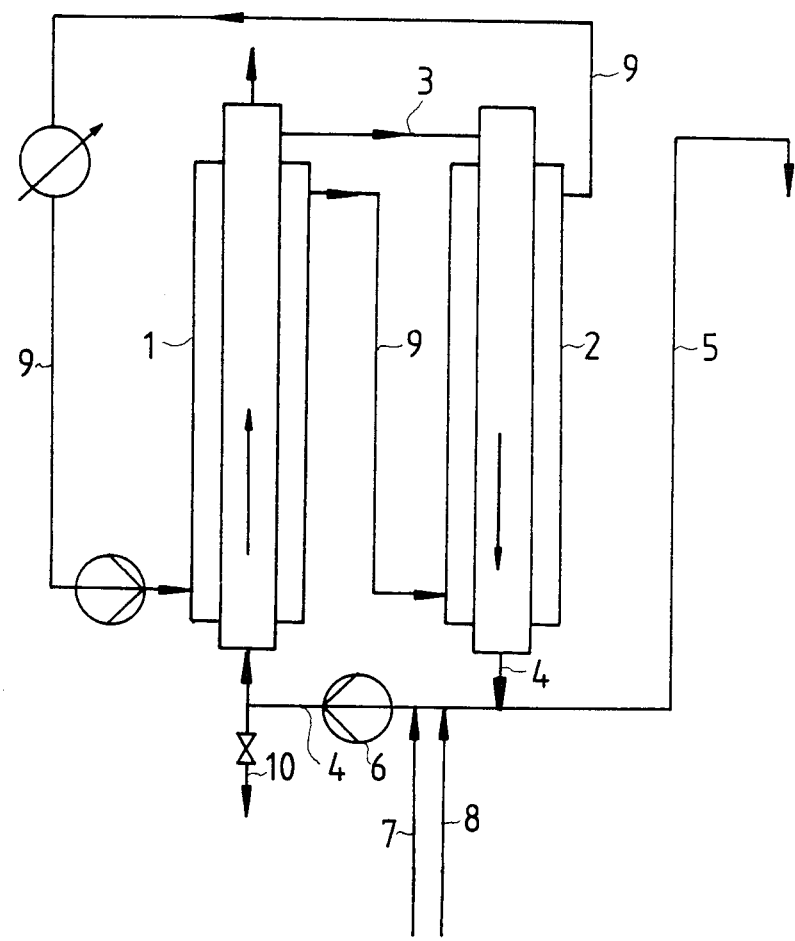

PROCESS FOR THE CONTINUOUS PRODUCTION OF 2-CARBOXYETHYL-ALKYL-PHOSPHINIC ACID DIALKYLESTERS

The present invention relates to a process for the continuous production of 2-carboxyethyl-alkyl-phosphinic acid dialkylesters.

2-carboxyethyl-alkyl-phosphinic acid dialkylesters are widely used as flameproofing agents or intermediate products for synthesizing plant protective agents.

As disclosed by V. K. Khairullin et al. (cf. Dokl. Akad. Nauk USSR 162, 827–828 and Zh. Obshch. Khim 36, pages 289–296), 2-carboxyethyl-alkyl-phosphinic acid dialkylesters can be made by reacting a 2-chloroformylethyl-alkyl-phosphinic acid chloride with an alcohol in the presence of a tertiary amine in accordance with the following reaction equation

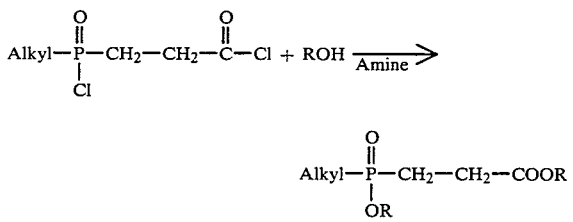

the final product being obtained in a yield of 50 to 60% of the theoretical.

The process described by A. N. Pudovik in Izv. Akad. Nauk USSR 1952, pages 902 to 907 enables the product to be obtained in improved yields. In this process, an alkanephosphonous acid monoalkylester is reacted with an acrylic acid alkylester in alcoholic solution and in the presence of a metal alcoholate, e.g. sodium alcoholate, as a catalyst, the resulting 2-carboxyethyl-alkyl-phosphinic acid dialkylester being obtained in a yield of 74% of the theoretical, provided that the alkyl group of the ester radicals is a $C_4H_9$ radical.

As results from the disclosure by Pudovik, the reaction just described occurs very violently upon the addition of the catalyst solution to the feed materials, and the reaction mixture becomes very hot. In other words, this process cannot be used for the commercial manufacture of the product.

It is therefore highly desirable to modify the process described by Pudovik so as to permit phosphinic acid dialkylesters to be produced on a commercial scale in improved yields.

The present invention relates more particularly to a process for the continuous production of 2-carboxyethyl-alkyl-phosphinic acid dialkylesters of the following general formula I

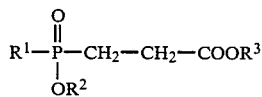
(I)

by reacting an alkanephosphonous acid monoalkylester of the following general formula II

with an acrylic acid ester of the following general formula (III)

$$CH_2=CH-COOR^5 \quad (III)$$

in the presence of a metal alcoholate of the formula $(R^6O)_nMe$ and an alcohol of the formula $R^7OH$, in which formulae
$R^1$ stands for an alkyl group having from 1 to 3 carbon atoms,
$R^2$ through $R^7$ each stand for an alkyl group having from 1 to 6 carbon atoms, and
Me stands for the metals
Li, Na, K where n is 1
Mg where n is 2 and
Al where n is 3
which comprises:

(a) introducing a quantity by volume (corresponding to the reactor volume) of the 2-carboxyethyl-alkyl-phosphinic acid dialkylester (to be produced), if desired in admixture with an alcohol corresponding to the metal alcoholate as a solvent into a reactor adapted to circulate reaction mixture therein, closed in itself and provided with cooling means and an overflow, and circulating the mixture in the reactor;

(b) continuously introducing the alkanephosphonous acid monoalkylester, acrylic acid alkylester and an alcoholic solution of the metal alcoholate into the reactor while cooling the material circulated therein, and reacting the whole at a temperature of about 0° to 80° C. within a period of about 5 to 120 minutes, the alkanephosphonous acid monoalkylester and acrylic acid alkylester being used in a molar ratio of about 1:0.9–2, and the metal alcoholate being used in a proportion of about 0.1 to 5 mol %, based on the phosphonous acid monoalkylester; and (c) continuously removing a mixture containing final product through the overflow of the reactor and distillatively separating 2-carboxyethyl-alkyl-phosphinic acid dialkylester from the mixture.

Further preferred and optional features of the present invention provide:
(a) for the reaction to be effected at a temperature of 20° to 50° C.,
(b) for the reactor to be charged with the reactants and catalyst solution, e.g. in the following manner
  (i) alkanephosphonous acid monoalkylester, acrylic acid alkylester and alcoholic solution of the metal alcoholate are introduced separately into the reactor or
  (ii) a mixture of alkanephosphonous acid monoalkylester and acrylic acid alkylester is introduced separately from the alcoholic solution of the metal alcoholate into the reactor or
  (iii) a mixture of the alkanephosphonous acid monoalkylester and alcoholic solution of the metal alcoholate is introduced separately from the acrylic acid alkylester into the reactor;
(c) for the alkanephosphonous acid monoalkylester and acrylic acid alkylester to have identical or different ester groups;

(d) for the alcoholic component of the metal alcoholate to correspond to the alcoholic component of the alkanephosphonous acid monoalkylester or to that of the acrylic acid alkylester;

(e) for the alkanephosphonous acid monoalkylester and acrylic acid alkylester to be used in a molar ratio of 1:1–1.3, for the catalyst to be used in a proportion of 1 to 5 mol %, based on the phosphonous acid monoalkylester, and (f) for the alcohol used as the solvent to be employed in a proportion of 0.1 to 1 mol per mol alkanephosphonous acid monoalkylester.

The alcohol used as the solvent e.g. for the metal alcoholate is absolutely necessary as it contributes to obtaining the final product in high yields.

In those cases in which a phosphonous acid ester and acrylic acid ester having different ester groups and an alcoholic metal alcoholate solution corresponding to these ester groups used, a product mixture is obtained as final product.

The present process enables 2-carboxyethyl-alkyl-phosphinic acid dialkylester to be produced continuously on a commercial scale in a yield of approximately 90% of the theoretical, i.e. in a yield not obtainable heretofore as far as we are aware.

The process will now be described with reference to the accompanying drawing and in the following Examples which illustrate the invention.

EXAMPLE 1

Preparation of 2-carboxyethyl-ethyl-phosphinic acid diethylester ($R^1=R^2=R^3=C_2H_5$)

A circulation reactor with a capacity of 1 liter comprising two jacketed tubular structures 1 and 2 which were connected together by means of lines 3 and 4, respectively, was filled with a mixture of 1000 g(4.50 mols) 2-carboxy-ethyl-ethyl-phosphinic acid diethylester to be produced and 62 g (1.35 mols) ethanol, up to the level of overflow 5. By means of pump 6, a mixture of 732 g (6.00 mols) ethanephosphonous acid monoethylester and 600 g (6.00 mols) ethyl acrylate was introduced per hour through line 7, and a solution of 16.8 g (0.20 mol) potassium ethylate in 120 g (2.61 mols) ethanol was introduced per hour through line 8, the reaction mixture being maintained at a temperature of 40°–42° C. by means of a cooling water cycle 9. Crude product flowing over through line 5 was collected over a period of 30 hours. It and the product taken from the reactor through line 10 after operation had been stopped gave a total of 45.1 kg. Low boiling matter was distillatively separated under water jet vacuum and filtered. Next, the product was distilled in a thin layer evaporator under vacuum and 37.17 kg (167.4 mols) 2-carboxy-ethyl-ethyl-phosphinic acid diethylester was obtained. After deduction of the quantity initially admitted to the reactor, the yield was 90.5% corresponding to an output of about 1200 g/l per hour.

EXAMPLE 2

Preparation of a methyl/isobutyl-ester mixture of 2-carboxyethyl-methyl-phosphinic acid ($R^1=CH_3$; $R^2$, $R^3=CH_3$ and i-$C_4H_9$)

The circulation reactor of Example 1 was filled with 1080 g (6.00 mols) 2-carboxyethyl-methyl-phosphinic acid dimethylester and 67 g (2.09 mols) methanol up to the level of the overflow. Next, a mixture of 680 g (5.00 mols) methanephosphonous acid monoisobutylester, 100 g (3.13 mols) methanol and 10.8 g (0.20 mol) sodium methylate were introduced per hour while cooling and also 470 g/h (5.60 mols) methyl acrylate through a separate line, the reaction mixture being maintained at a temperature of 24°–26° C. by cooling from the outside. The reaction was stopped after 24 hours and a total quantity of 31.4 kg crude product (product coming continuously from the overflow and product taken from reactor, after stoppage) was worked up as described in Example 1. Altogether 24.89 kg ester mixture was obtained. It was analyzed gas-chromatographically and found to be composed as follows:

Dimethylester: 33.3 wgt % corresponding to 46.05 mols
Methyl/isobutyl esters: 47.2 wgt % corresponding to 59.92 mols
Diisobutylester: 19.5 wgt % corresponding to 18.38 mols.

After deduction of the quantity of dimethylester initially admitted to the reactor, the yield was 92.8% corresponding to an output of about 1000 g/l.

We claim:

1. In the process for the continuous production of 2-carboxyethyl-alkyl-phosphinic acid dialkylesters of the following general formula I

by reacting an alkanephosphonous acid monoalkylester of the following general formula II

with an acrylic acid ester of the following general formula III

in the presence of a metal alcoholate of the formula $(R^6O)_n Me$ and an alcohol of the formula $R^7OH$, in which formulae $R^1$ stands for an alkyl group having 1 to 3 carbon atoms, $R^2$ through $R^7$ each stand for an alkyl group having from 1 to 6 carbon atoms, and Me stands for the metals Li, Na, K where n is 1
Mg where n is 2 and
Al where n is 3 the improvement which comprises:

(a) introducing a quantity by volume (corresponding to reactor volume) of the 2-carboxyethyl-alkyl-phosphinic acid dialkylester (to be produced), as a solvent into a reactor adapted to circulate reaction mixture therein, closed in itself and provided with cooling means and an overflow, and circulating the mixture in the reactor;

(b) continuously introducing the alkanephosphonous acid monoalkylester, acrylic acid alkylester and an alcoholic solution of the metal alcoholate into the reactor while cooling the material circulated therein, and reacting the whole at a temperature of about 0° to 80° C. within a period of about 5 to 120 minutes, the alkanephosphonous acid monoalkylester and acrylic acid alkylester being used in a molar ratio of about 1:0.9–2, and the metal alcoholate being used in a proportion of about 0.1 to 5 mol %, based on the phosphonous acid monoalkylester; and (c) continuously removing a mixture containing final product through the overflow of the reactor and distillatively separating 2-carboxyethyl-alkyl-phosphinic acid dialkylester from the mixture.

2. The process as claimed in claim 1, wherein the reaction is effected at a temperature of 20° to 50° C.

3. The precess as claimed in claim 1, wherein
(a) the alkanephosphonous acid monoalkylester, acrylic acid alkylester and alcoholic solution of the metal alcoholate are introduced separately into the reactor or
(b) a mixture of the alkanephosphonous acid monoalkylester and acrylic acid alkylester is introduced separately from the alcoholic solution of the metal alcoholate into the reactor or
(c) a mixture of the alkanephosphonous acid monoalkylester and alcoholic solution of the metal alcoholate is introduced separately from the acrylic acid alkylester into the reactor.

4. The process as claimed in claim 1, wherein the alkanephosphonous acid monoalkylester and acrylic acid alkylester have identical or different ester groups.

5. The process as claimed in claim 1, wherein the alcoholic component of the metal alcoholate corresponds to the alcoholic component of the alkanephosphonous acid monoalkylester and acrylic alkylester, respectively.

6. The process as claimed in claim 1, wherein the alkanephosphonous acid monoalkylester and acrylic acid alkylester are used in a molar ratio of 1:1–1.3 and the metal alcoholate is used in a proportion of 1 to 5 mol %, based on the phosphonous acid monoalkylester.

7. The process as claimed in claim 1, wherein 0.1 to 1 mol alcohol is used as the solvent per mol alkanephosphonous acid monoalkylester.

8. The process as claimed in claim 1, wherein said solvent comprises, in admixture, said 2-carboxyethyl-alkyl-phosphinic acid dialkylester and an alcohol corresponding to the metal alcoholate.

* * * * *